United States Patent [19]

Guillemin

[11] Patent Number: 4,785,660
[45] Date of Patent: Nov. 22, 1988

[54] PROCESS AND INSTALLATION FOR ON-LINE ANALYSIS OF A LIQUID PRODUCT BY LIQUID PHASE CHROMATOGRAPHY

[75] Inventor: Claude Guillemin, Paris, France

[73] Assignee: Rhone-Poulenc Recherches, Courbevoie Cedex, France

[21] Appl. No.: 24,177

[22] Filed: Mar. 10, 1987

[30] Foreign Application Priority Data

Apr. 25, 1986 [FR] France ................ 86 06228

[51] Int. Cl.4 ............................................. G01N 15/00
[52] U.S. Cl. .................................... 73/61.1 C; 422/70
[58] Field of Search ............ 73/61.1 C, 23.1, 863.86; 422/70; 436/161; 210/198.2, 656, 659, 663

[56] References Cited

U.S. PATENT DOCUMENTS

| | | | |
|---|---|---|---|
| 3,860,393 | 1/1975 | Campen, Jr. ................ | 436/161 |
| 3,966,411 | 6/1976 | Ross et al. ................ | 436/161 |
| 4,186,607 | 2/1980 | Porter et al. ................ | 73/61.1 C |
| 4,229,971 | 10/1980 | Ririe, Jr. ................ | 436/161 |
| 4,472,354 | 9/1984 | Passell et al. ................ | 436/161 |

FOREIGN PATENT DOCUMENTS 2412106 7/1979 France .
2491215 4/1982 France .

Primary Examiner—Tom Noland
Assistant Examiner—Hezron E. Williams
Attorney, Agent, or Firm—Burns, Doane, Swecker & Mathis

[57] ABSTRACT

This invention relates to a process and installation for on-line analysis of a liquid product by liquid phase chromatography, the device for carrying out the process including a sampling and treatment probe disposed within the product and a chromatograph associated with the probe. An eluate detector disposed remote from the chromatograph and a monitoring unit takes into account the variations of appearance of a noteworthy peak with respect to the same peaks of an earlier chromatogram.

14 Claims, 4 Drawing Sheets

PROCESS AND INSTALLATION FOR ON-LINE ANALYSIS OF A LIQUID PRODUCT BY LIQUID PHASE CHROMATOGRAPHY

FIELD OF THE INVENTION

The present invention relates to the technical domain of on-line analysis, by liquid phase chromatography, of samples taken periodically from a medium in the course of an industrial process. The periodic taking of samples and the qualitative and/or quantitative analysis thereof make it possible to follow the advance of a chemical reaction or of a physical operation and consequently to make, either manually or automatically, modifications in the operating conditions of the installation in order to follow as closely as possible the specifications previously defined for obtaining products of slightly variable or constant characteristics.

The technical domain concerned is more particularly that of heterogeneous liquid media, such as dispersions of solids, liquids or gases in a continuous liquid phase.

BACKGROUND OF THE INVENTION

In automatic industrial on-line analysis by liquid phase chromatography, a sample is taken from the liquid medium to be analyzed, with the aid of a probe, and this sample is conveyed by means of at least one pump through a circulation circuit or sampling line comprising tubes, filters, valves, connections, etc . . . Such a circuit is intended to take the sample towards a chromatograph in liquid phase located geographically at a certain distance from the point of sampling.

This technique is generally satisfactory when the liquid medium to be analyzed is homogeneous. On the other hand, in the case of taking a sample in a heterogeneous medium comprising, for example, a solid or polymeric phase dispersed in a liquid, clogging, fouling, blocking and even seizure of mobile elements of the sampling line very often occur. Such incidents result in a loss of reliability and credibility of the analysis effected and, furthermore, considerably increase maintenance of the analysis device or installation.

In an attempt to minimize this constraint, it is usually sought to reduce the length of the sampling line by recommending an installation of the type shown in FIG. 1, which represents the known state of the art. In this Figure, an on-line analysis installation comprises means 1 for taking and filtering a sample from a vessel 2 for storage or reaction of the liquid product 3 to be analyzed. Means 1 are connected by a sampling line 4 to an analysis unit 5 which is generally disposed on the site of the vessel 2, so as to reduce as much as possible the length of this line 4. The analysis unit 5 comprises means for injecting the sample and the liquid vector fluid by pump 6, one or more separation columns and detection means. The unit 5 is electrically connected to a remote monitoring unit 7 which assesses the results of analysis and controls the modification of the operational parameters of the industrial process as a function of the analytic characteristics noted.

For such an installation to operate satisfactorily, it is know that the analysis must be carried out under constant conditions of temperature and of flowrate of the vector fluid. Now, by placing the analysis unit 5 as close as possible to the site of the vessel 2, it is readily appreciated that the variations in temperature of the industrial premises will have a detrimental influence on the development of the analysis sequences. This is why it is usual to construct the unit 5 in the form of a temperature-regulated assembly.

In reality, such means lead to an installation which is particularly delicate to operate, is expensive and of which the maintenance must necessarily be carried out by highly qualified personnel. In addition to this negative aspect, it should be noted that the means recommended do not make it possible to eliminate completely the sampling line 4 of which the drawbacks set forth hereinabove remain.

It should also be pointed out that the existence of a relatively long sampling line 4 most often involves a continuous taking and treatment of samples, this on the one hand representing a considerable consumption of the liquid medium to be analyzed and, on the other hand, poses a problem of evacuation of this continuous sampling when it is question of a product of polluting or non-recycyable nature.

OBJECTS AND SUMMARY OF THE INVENTION

It is an object of the invention to propose a novel process and device which are particularly designed to reduce the length of a sampling line 4 and to eliminate the connections, valves, filters and other sources of clogging, so as to eliminate the drawbacks mentioned hereinabove.

The object of the invention proposes to produce, in a substantially unitary form, both the sampling, treatment and analysis means and to take advantage of the instability provoked by the fluctuations in temperature and flowrate of the vector fluid, by proposing a novel process for searching, recognizing and measuring the peaks of the separated eluates, based on a taking into account of known characteristics taken from a chromatogram or a collection of earlier chromatograms relating to samples of the same product.

In other words, the recommended process is based on taking into account the instability of the parameters, this corresponding to a step opposite that of the prior art. The process of the invention aims at proposing search, recognition and measuring means which automatically adapt themselves to the variations in temperature and flowrate likely to be imposed on the liquid vector fluid by the operational conditions and by the variation in temperature of the surrounding medium in which the sampling, treatment and analysis unit and the vessel containing the product to be analyzed are located.

To attain the objects set forth hereinabove, the process according to the invention is characterized in that it consists in:

taking and treating the sample of the product to be analyzed by a sampling and treatment head placed within said product;

transferring the sample thus treated into a chromatograph associated with the sampling head;

establishing on-line the chromatogram of the sample;

selecting, from a prior chromatogram of the same product made under given conditions of temperature and of flowrate, a noteworthy peak of a known component and measuring the position of this peak in relation with the origin of the corresponding sequence of analysis, in order to define a term of comparison;

searching in the chromatograph of the present sample the position of the same noteworthy peak;

measuring the difference in position between the term of comparison and the peak of the analysis underway, in order to extract therefrom a correction factor of known magnitude and sign;

allocating this correction factor to the search and recognition of position of the other different peaks of the chromatogram;

and proceeding in this way for each successive analysis of the same product in order to adapt the search and recognition of the peaks as a function of the variations in temperature and flowrate of the liquid vector fluid employed for effecting analysis.

The invention also has for its object a device for carrying out the above process, said device characterized in that it comprises:

as sampling member, a sampling and treatment probe disposed within the product to be analyzed;

a chromatograph associated with the probe;

a detector of eluates placed remote from the chromatograph;

and a montoring unit comprising a calculating machine taking into account, upon each successive analysis of the same product, at least the variations in appearance of a noteworthy peak with respect to the same peak of an earlier chromatogram of the same product, to calculate a difference in appearance, extract therefrom a correction factor applied to the search and recognition of the other different peaks of the chromatogram of the sample in the course of analysis.

BRIEF DESCRIPTION OF THE DRAWINGS

The invention will be more readily understood on reading the following description with reference to the accompanying drawings, in which.

DETAILED DESCRIPTION OF A PREFERRED EMBODIMENT

Figure 1:
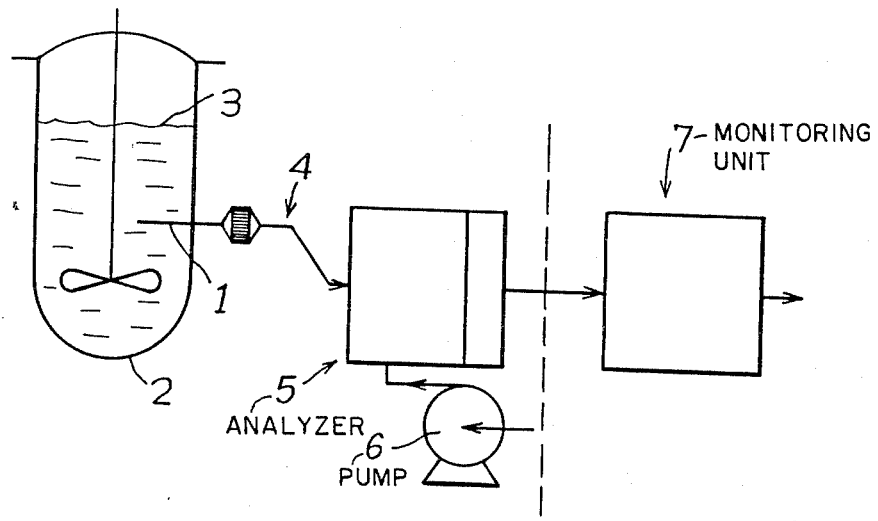
FIGS. 1 and 2 are schematic views illustrating, comparatively, an installation of the conventional type and an installation for on-line analysis of a liquid product by liquid phase chromatography according to the invention.
Figure 2:
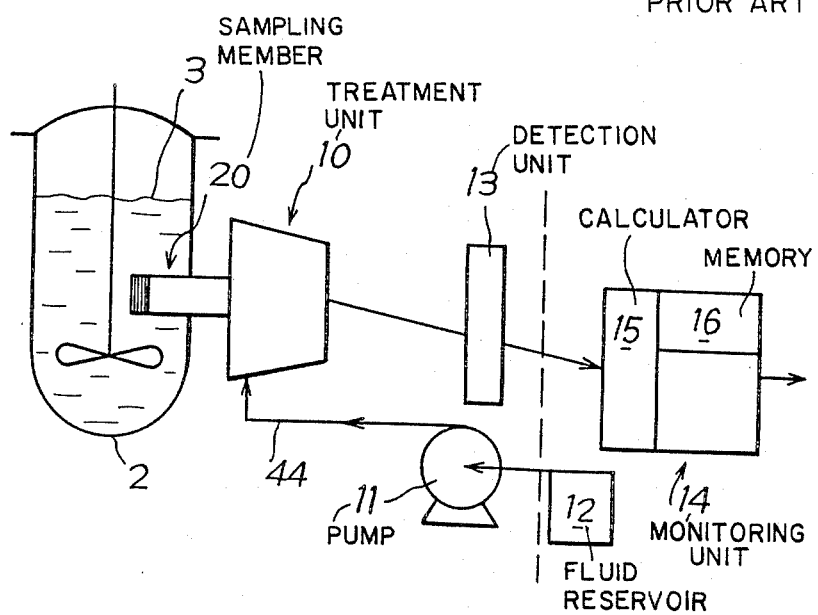

Referring again to the drawings, FIG. 2 shows an installation for carrying out the process of the invention. In this Figure, the installation comprises a sampling, treatment and analysis assembly 10 which is strictly speaking located in direct relation with the vessel 2. This unit 10 is supplied by a pump 11 with liquid vector fluid taken from a reservoir 12. The unit 10 is connected from a distance to detection means 13 themselves connected to a monitoring unit 14 placed in monitoring premises generally situated away from the site where the vessel 2 is located. The monitoring unit 14 comprises a calculating machine 15 for managing the analytic information furnished by the means 13, according to an automatically adapting comparative process from a chromatograph of a collection of chromatograms sotred in a memory 16.

The concept of the installation according to the present invention therefore consists in providing, directly on the vessel 2, the implantation of an assembly 10 adapted to be at least partly immersed in the medium 3 to be analyzed, so as to ensure sampling and physical treatment of a sample analysed immediately on-line by a chromatograph not presenting any temperature regulation system.

Figure 3:
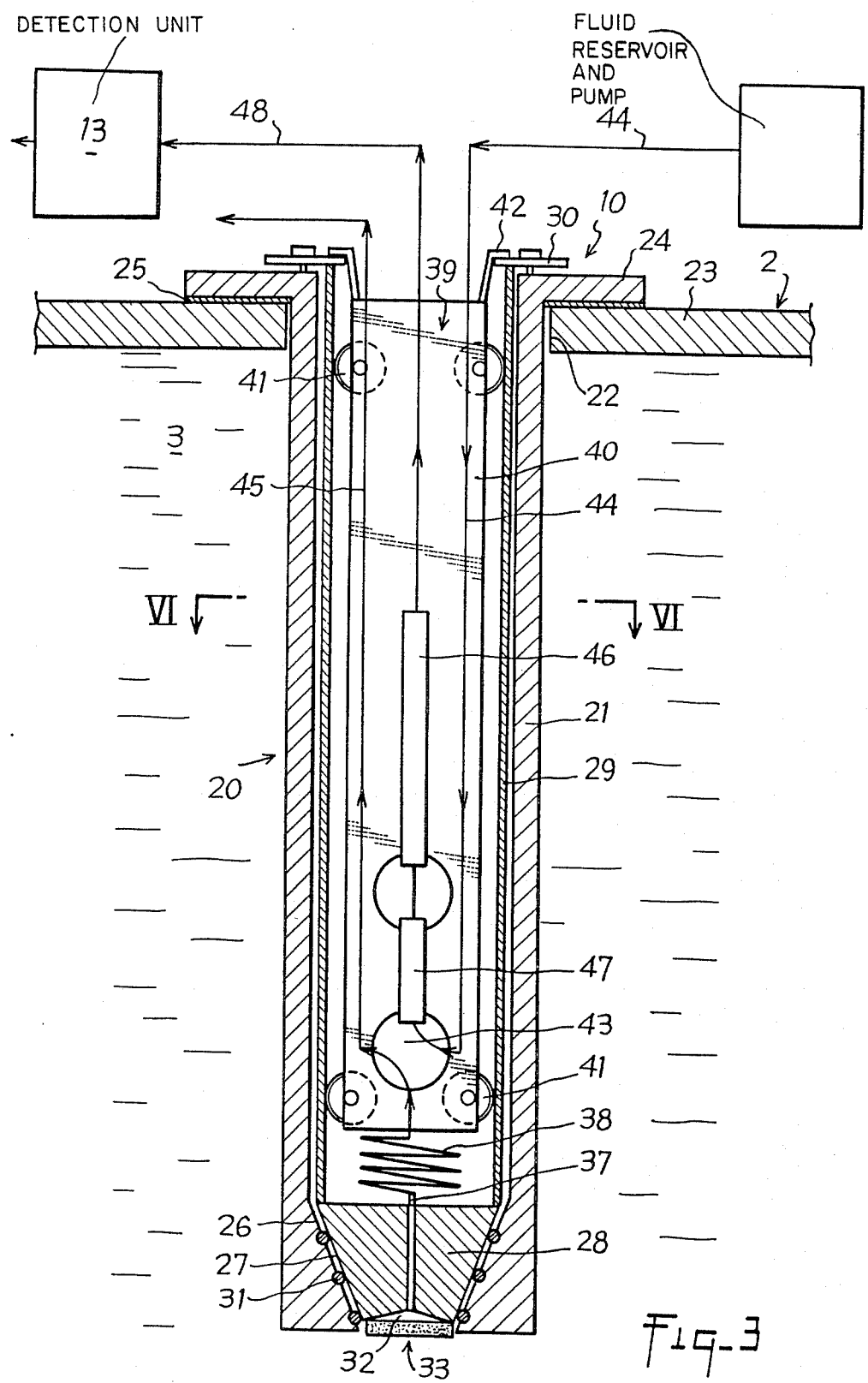
FIG. 3 is an elevational section of one of the elements constituting the device for carrying out the process.

The assembly 10, shown more particularly in FIG. 3, comprises a sampling member 20, constituted in the form of a probe. This sampling member 20 comprises a cylindrical tubular body 21 adapted to be mounted in and fitting with seal through a hole 22 in the wall 23 of the vessel 2, so as to plunge in the liquid product 3 to be analyzed. To this end, one of the ends of the cylindrical tubular body 21 comprises a flange 24 ensuring removable fit and holding of a seal 25, under suitable conditions.

The cylindrical tubular body 21 comprises a seat 26, for example truncated, intended for supporting a complementary bearing surface 27 formed by a sampling and treatment head 28 provided at the end of a tubular lining 29 included in the body 21 which bears it. The head 28 is preferably constituted by an independent machined part added to the end of the lining 29 of which the other end is provided with fixation members 30 adapted to immobilize the lining 29 axially inside the cylindrical tubular body 21. The fixation members 30 are also designed so as to constitute members for stressing seals 31, for example of the O-ring type, interposed between the seat 26 and the complementary bearing surface 27.

Figure 4:
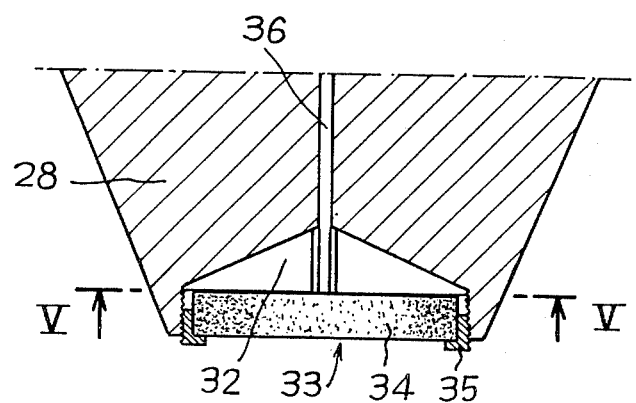
FIG. 4 is a partial transverse section, on a larger scale, of a detail of construction.
Figure 5:
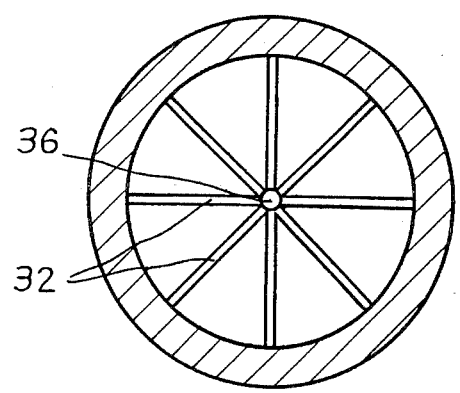
FIG. 5 is a transverse section taken substantially along line V—V of FIG. 3.

The sampling head 28 is machined so as to comprise, from its face substantially flush with the corresponding end of the body 21, hollows 32 for collection, for example substantially radical, as illustrated in FIGS. 4 and 5. The hollows 32 are covered by a physical treatment element 33 such as a filtration or ultra-filtration element, preferably removable. The element 33 may be constituted by a membrane or a pellet 34, of any appropriate nature, particularly sintered material immobilized by a removable ring 35, for example screwed.

The hollows 32 communicate with a central conduit 36 opening inside the sampling head 28. The conduit 36 is associated with means 37 for connection with a tube 38, preferably constituted by a supple element, of the capillary type pre-wound helically in the state of rest. The conduit 36 and the tue 37 constitute the sampling line.

Figure 6:
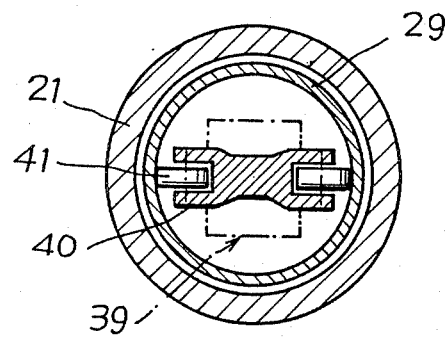
FIG. 6 is a transverse section taken substantially along line VI—VI of FIG. 3.

According to a preferred embodiment, the assembly 10 comprises, in addition to probe 20, a chromatograph 39 which is preferably incorporated in the probe 20. In the example illustrated, the chromatograph 39 comprises (FIGS. 3 and 6), a fixation and support plate 40 which is mounted, via centering rollers 41 or other means, axially mobile inside the lining 29, which it constitutes, to some extent, a diametral core. The plate 40 is associated with stops 42 provided to cooperate, particularly with the fixation members 30, so as to immobilize the plate axially in complete insertion inside the lining 29.

The plate 40 supports, on one or on two of its faces, the elements consituting a liquid phase chromatograph. Such elements comprise an injection valve 43, for example of the fourway type, of which one of the inlets is connected to the tube 38. The other inlet of the injection valve 43 is connected to a tube 44 for supplying liquid vector fluid and issuing from the outlet of the pump 11. One of the outlets of the injections valve 43 is connected to a suction pipe 45, necessary in the case of the liquid product 32 being stored or contained in the vessel 2 without being subjected to a containment pressure. The other outlet of the injection valve 43 is connected to a separation column 46, possibly associated with a pre-column 47, and of which the outlet is connected by a remote pipe 48 to the detector 13.

The assembly 10 is characterized by its structural compactness and by the implantation, within the medium 3 to be sampled, of the sampling and treatment head 28 which makes it possible to carry out directly in situ the physical treatment by filtration or ultrafiltration of the sample to be taken. This sample is collected by the hollows 32 either via the pressure prevailing in the vessel 2, or via suction means in relation with the pipe 45.

This form of construction makes it possible to reduce to a minimum the length of the sampling line between the point of sampling and the injection valve 43, being given that this latter is at best incorporated inside the probe 20. In such a case, the length of the sampling line corresponds solely to the length of the tube 38 necessary to allow, if need be, the axial displacement of the plate 40, with a view to extraction thereof with respect to the lining 29.

This embodiment makes it possible to eliminate the bends, connections, filters and all the members responsible for a poorer circulation likely to generate clogging and blocking and which increase the analysis time.

However, it must be considered that an equivalent result may be obtained if the chromatograph 39 is disposed outside the probe 20, being placed at a short distance therefrom.

Furthermore, being given that the sampling and treatment head 28 is located directly within the liquid medium to be sampled, there is a possibility of automatic unclogging of the filtration or ultra-filtration element 33 solely by the means for maintaining the liquid product 3 stirred or in circulating, as is generally the case in the industrial installations for production or storage of intermediate or finished products.

It will be appreciated that, although this form of construction makes it possible to effect a pseudo-conditioning of temperature of the chromatograph 39 which is subjected to the influence of the temperature of the surrounding medium, i.e. the product 3, this does not apply, on the other hand, to the liquid vector fluid transiting through the pump 11 and the supply pipe 44. Such a vector fluid will therefore necessarily be subjected to the temperature variations of the site in which the vessel 2 is implanted and corollary flowrate variations will consequently be imposed thereon.

So as not to be penalized by these variations which would eliminate the possibility of implantation in situ of the sampling and analysis assembly 10, the process of analysis according of the invention employs, in the monitoring unit 14, the calculating machine 15 of which the program is fixed to effect automatic compensation of its variations in temperature and flowrate.

Figure 7:
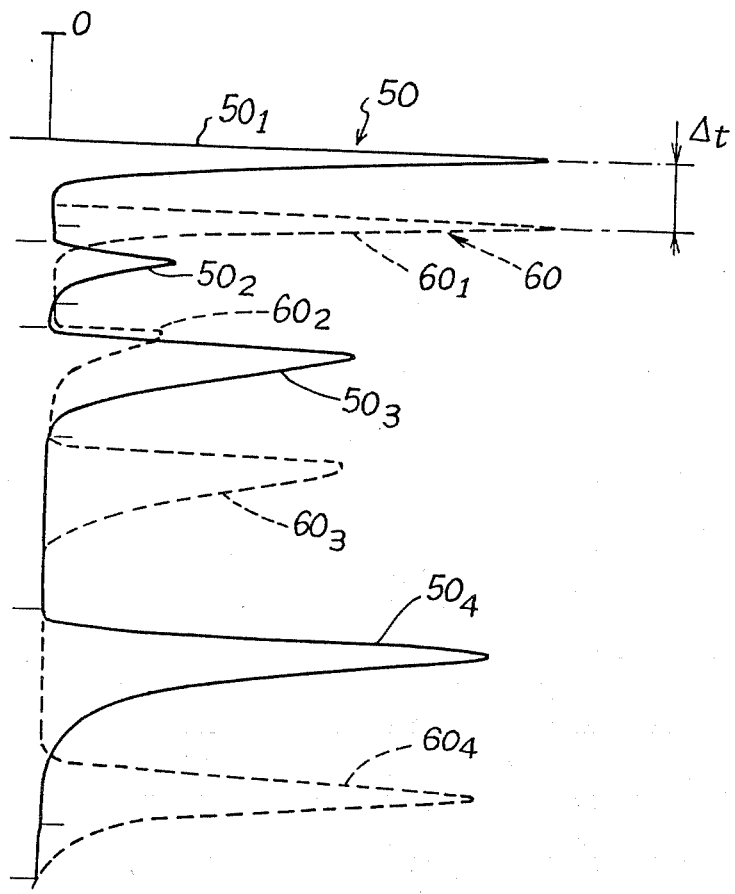
FIG. 7 is a schematic curve illustrating one of the characteristics phases of the process of the invention.

In order to perform this function, the control program of the calculating machine 14 is set up to ensure search and qualitative recognition of the different peaks corresponding to the different separated eluates, by proceeding in the following manner, as illustrated in FIG. 7.

In accordance with this Figure, a chromatogram 50 of a sample of the product 3 comprises a certain number of peaks, such as those shown in solid lines and bearing, respectively, references $50_1$ to $50_4$. Such a chromatogram, corresponding to the analysis of a sample of product 3 effected under conditions considered appropriate, is stored in the memory 16, so as to constitute a reference basis for assessing a subsequent chromatogram. It may therefore be question of a chromatogram 50 corresponding, at first, to optimum conditions of analysis or, as will be seen in the following, of the last chromatogram effected on the basis of a sample of the same product.

When the chromatogram corresponding to the sample in the course of analysis is furnished to the calculating machine 15, such as the one shown in broken lines in FIG. 7 and designated by general reference 60, said calculating machine selects a noteworthy reference peak, always found and preferably standing out from the other peaks. By way of example, this peak may be the one designated by reference $60_1$. The calculating machine then seeks the presence of the same peak in the reference chromatogram 50 in order to recognize it and to be able to determine whether these two peaks, for example $60_1$ and $50_1$, are placed at the same distance from the origin of injection O or whether, on the contrary, these two peaks are offset in one direction or in the other relatively. If the calculating machine detects no shift, this signifies that the conditions of analysis for the sample underway are identical to those of the preceding analysis and that consequently it is possible to find and recognize, at the same places on the chromatogram from the origin O, the same characteristics peaks of interest of the different eluates separated.

If, on the other hand, the calculating machine detects a shift, it measures the difference $\Delta_t$ either between the thresholds of appearance or, for example, between the summits of the peaks $60_1$ and $50^1$. The calculating machine takes this measurement $\Delta_t$ into account for effecting a corresponding correction in the search and recognition of the other different peaks of interest $60_1$ to $60_3$ which may thus be easily identified and validated, even if their surface has ben modified by the modification of the conditions of analysis. The different peaks of interest are thus recognized by their relative retention time with respect to the reference peak, retention time corrected by the factor $\Delta_t$ which is allocated according to its sign to one of the lower or upper terminals of a temporal detection window applied by the machine to the analysis of the chromatogram. The shift of the corresponding terminal will either be constant for all the peaks to be recognized and validated, or be increased by a certain value as a function of the increasing retention time of the peaks. The new retention times of the peaks are stored for the next sequence.

The calculating machine may then effect the quantitative measurement of the different peaks recognized, then validated by proceeding in known manner by a comparative method.

By so taking into account the corrective factor $\Delta_t$, the calculating machine 15 automatically adapts itself to the variations in temperature and flowrate of the liquid vector fluid and is able to recognize and validate the different peaks having to be sought then measured.

Quantative measurement of the peaks may also be based on the known concept of the "deferred standard" consisting in the injection of a third pure compound in each analytic sequence, this injection being deferred with respect to that of the sample, so that the corresponding peak does not interfere with the peaks of the sample. The peak of the deferred standard may serve as pre-reference or reference according to the process which has just been described.

In the embodiment of this quantitative method, the peak corresponding to the deffered standard is not recognized by its retention time, but by its previously stored area. When the peak has thus been recognized, the calculations of concentration of the different eluates by measuring the areas of the corresponding peaks are effected with respect to the area of the peak of the "deferred standard".

However, it will be understood that if there is evolution of the retention times of the peaks of the sample, it is necessary consequently to adjust the injection time of the deferred standard in order to avoid interference of the peaks. According to the invention, such adjustment is effected by the machine 15 which applies, at the injection time, the amplitude and the sign of the corrective factor $\Delta_t$ to any time function which regulates the analytic sequence, such as injection of the deferred standard and also any possible commutation of column, the final time of the analytic sequence and the injection time of the following sequence or, more generally, any outside function, this making it possible for example to control valves on the sampling or on the reactor, etc ..

The variations in flowrate of the liquid vector fluid, due for example to the variations in temperature, substantially influence the detection means 13 which may then furnish an unstable response. If the area of the peak of the deferred standard varies for such reasons by more than a certain percentage with respect to the area of the same peak of the preceding analysis according to the process of the invention, a second injection of deferred standard is triggered off, in the sequence underway, by selecting the injection time in order to avoid interference of peaks. The surface basis retained for the quantitative measurement of the peaks of the eluates will then be the average area between the areas of the two peaks of the two injections of deferred standard.

By way of example, a concentration of 0.6% by weight of phenol in a mixture containing hydroquinone and pyrocatechol (0.38% of hydroquinone and 0.25% of pyrocatechol in water) is dosed with a repeatability of 1.5% with a stable flowrate.

A fluctuation of the flowrate of 25% is then provoked, which should be translated by an error of the same amplitude on the dosage of the phenol. It will be observed that, thanks to the process of the invention, the response is validated with a maximum error of 7%.

This example illustrates the interest of the present invention.

As shown by the foregoing, the use of as assembly for sampling and treatment in situ and for analysis, non-thermostated or temperature regulated, makes it possible, by the process of comparative assessment described hereinabove, to design an installation having a short response time at its disposal and furnishing results of analysis which automatically take into account the variations in temperature and flowrate of the liquid vector fluid injected. Such an installation is therefore of smaller dimensions and lower cost compared with the prior art.

In addition, the fact of placing the sampling, treatment and analysis assembly 10 within the product to be analyzed reduces the quantity of sample having to be continuously taken and allows a reduction of the duration of stagnation or of containment of the sample in the sampling line, which promotes obtaining of chromatograms of more substantially constant characteristics.

The invention is not limited to the examples described and shown, as various modifications may be made thereto without departing from the scope thereof.

What is claimed is:

1. Apparatus for on-line analysis of a liquid product by liquid phase chromatography, comprising:
   sampling and treatment means disposed within said product to be analyzed for taking and treating a sample thereof,
   a chromatograph,
   means for transferring said sample to said chromatograph,
   means for establishing on-line a chromatogram of said sample,
   means for selecting a noteworthy peak from a reference chromatogram of the same product made under given conditions of temperature and flow rate;
   means for comparing the relative positions of corresponding noteworthy peaks on said reference chromatogram and sample chromatogram, respectively,
   means for determining a correction factor in accordance with any difference between said positions, and
   means for applying said correction factor to other peaks of said sample chromatogram.

2. Apparatus according to claim 1, wherein said noteworthy peaks selected correspond to a known component of the product.

3. Apparatus according to claim 1, wherein said sampling and treating means comprise a sampling probe disposed in said product, said chromatograph being disposed within said sampling probe.

4. Apparatus according to claim 3, wherein said sampling probe comprises a cylindrical body extending through a wall of a vessel containing said product, a removal treatment element mounted on an inner end of said body, said body comprising a seat adjacent said treatment element, a sampling and treatment head disposed in said body and sealingly abutting said seat, said head including passages disposed behind said treatment element for collecting a sample of said product, and a sampling line connecting said passages to said chromatograph.

5. Apparatus according to claim 4, wherein said chromatograph is disposed within said probe behind said head.

6. Apparatus according to claim 3 including a removable fixation ring for mounting said treatment element on said head.

7. Apparatus according to claim 6, wherein a tubular lining is connected to said head, said chromatograph being mounted on a mobile core movably disposed in said lining.

8. Apparatus according to claim 7, wherein said chromatograph comprises at least one separation column, there being provided a conduit for conducting liquid vector fluid to said chromatograph.

9. Apparatus according to claim 1, wherein said comparing means includes means for sensing relative shifts between said noteworthy peaks on said reference and sample chromatographs.

10. Apparatus according to claim 1, wherein said comparing means includes means for comparing the areas of said noteworthy peaks on said reference and sample chromatographs.

11. Apparatus according to claim 1, wherein said comparing means includes means for comparing the areas of noteworthy peaks on said sample chromatographs with areas of noteworthy peaks of a second reference chromatograph.

12. Apparatus for on-line analysis of liquid product by liquid phase chromatography comprising a vessel containing said liquid product, a probe disposed in said product and comprising a tubular means extending into said product, a sampling and treatment head disposed in said tubular means for collecting a sample of said product, a chromatograph disposed in said tubular means and communicating with said head for receiving said sample, and a detector of eluates operably connected to said chromatograph.

13. Apparatus according to claim 12, wherein said tubular means carries a seat, said head sealingly engaging said seat, a tubular liner extending rearwardly from said head, said chromatograph disposed movably within said liner, and passage means extending through said head for conducting said sample to said chromatograph.

14. Apparatus according to claim 12 including a filter element mounted at an inner end of said tubular means to define a treatment means.

* * * * *